US012692343B2

(12) United States Patent
Scheel et al.

(10) Patent No.: US 12,692,343 B2
(45) **Date of Patent: \*Jul. 28, 2026**

(54) PROCESS FOR PRODUCING FUNCTIONALIZED POLYTHIOPHENES

(71) Applicant: Heraeus Epurio GmbH, Hanau (DE)

(72) Inventors: Arnulf Scheel, Leverkusen (DE); Udo Merker, Leverkusen (DE); Reza Saadat, Leverkusen (DE)

(73) Assignee: HERAEUS EPURIO GMBH, Hanau (DE)

( * ) Notice: Subject to any disclaimer, the term of this patent is extended or adjusted under 35 U.S.C. 154(b) by 0 days.

This patent is subject to a terminal disclaimer.

(21) Appl. No.: 18/692,556

(22) PCT Filed: Jul. 25, 2022

(86) PCT No.: PCT/EP2022/070733
§ 371 (c)(1),
(2) Date: Mar. 15, 2024

(87) PCT Pub. No.: WO2023/041228
PCT Pub. Date: Mar. 23, 2023

(65) Prior Publication Data
US 2024/0376255 A1 Nov. 14, 2024

(30) Foreign Application Priority Data
Sep. 20, 2021 (EP) ..................................... 21197813

(51) Int. Cl.
*C08G 61/12* (2006.01)
*H01B 1/12* (2006.01)
(Continued)

(52) U.S. Cl.
CPC .......... *C08G 61/126* (2013.01); *H01B 1/127* (2013.01); *H01G 11/48* (2013.01); *C07D 495/04* (2013.01);
(Continued)

(58) Field of Classification Search
None
See application file for complete search history.

(56) References Cited

U.S. PATENT DOCUMENTS 7,497,879 B2 3/2009 Kakuma et al.
10,563,071 B2 2/2020 Tagawa et al.
(Continued)

FOREIGN PATENT DOCUMENTS

CN 106415759 A 2/2017
CN 111763305 A 10/2020
(Continued)

OTHER PUBLICATIONS

Kim Jeonghun et al, "Self-Doped Conjugated Polymerie Nanoassembly by Simplified Process for Optical Cancer Theragnosis", Advanced Functional Materials, vol. 25, No. 15, Feb. 26, 2015 (Feb. 26, 2015), pp. 2260-2269, XP055890745, DE ISSN: 1616-301X, DOI: 10.1002/ adfm.201500076.
(Continued)

*Primary Examiner* — Eli D. Strah
(74) *Attorney, Agent, or Firm* — Panitch Schwarze Belisario & Nadel LLP

(57) ABSTRACT

A process for producing a liquid composition comprising a functionalized π-conjugated polythiophenes, comprising the process steps of
i) providing a liquid phase comprising a functionalized π-conjugated polythiophene that is dissolved or dis-
(Continued)

persed in a solvent, wherein the functionalized π-conjugated polythiophene comprises repeating units of the general formula (I)

(I)

wherein

X, Y are identical or different and are O, S, or NR$^1$, wherein R$^1$ is hydrogen or an aliphatic or aromatic residue having 1 to 18 carbon atoms;

A is an organic residue carrying an anionic functional group;

and wherein the liquid phase has a pH-value of less than 2.5;

ii) adjusting the pH-value of the liquid phase provided in process step i) to a value in the range from 2.5 to 10 by the addition of a base.

The present invention also relates to a liquid composition obtainable by this process.

3 Claims, 4 Drawing Sheets

(51) Int. Cl.
*H01G 11/48* (2013.01)
*C07D 495/04* (2006.01)

(52) U.S. Cl.
CPC ................ *C08G 2261/1424* (2013.01); *C08G 2261/3223* (2013.01); *C08G 2261/43* (2013.01); *C08G 2261/71* (2013.01); *Y02E 60/13* (2013.01)

(56) References Cited

U.S. PATENT DOCUMENTS

| | | | |
|---|---|---|---|
| 10,767,003 B2 * | 9/2020 | Scheel | ...................... C25B 3/23 |
| 2004/0044214 A1 | 3/2004 | Andriessen | |
| 2015/0255221 A1 | 9/2015 | Asteman et al. | |
| 2018/0208713 A1 | 7/2018 | Scheel et al. | |

FOREIGN PATENT DOCUMENTS

| | | | | |
|---|---|---|---|---|
| DE | 10 2004 022674 A1 | 11/2005 | | |
| DE | 10 2005 043 828 A1 | 3/2007 | | |
| DE | 10 2009 007 594 A1 | 8/2010 | | |
| EP | 0 340 512 B2 | 11/1989 | | |
| EP | 1122274 A1 | 8/2001 | | |
| EP | 3037479 A1 | 6/2016 | | |
| EP | 3037497 A1 | 6/2016 | | |
| JP | 2015532525 A | 11/2015 | | |
| JP | 6131780 B2 | 5/2017 | | |
| JP | 2017222831 A | 12/2017 | | |
| JP | 2018507268 A | 3/2018 | | |
| JP | 2020007519 A | 1/2020 | | |
| JP | 2023016573 A | 2/2023 | | |
| WO | 2007066353 A2 | 6/2007 | | |
| WO | 2009/141209 A1 | 11/2009 | | |
| WO | WO-2010003874 A2 * | 1/2010 | .......... | H01G 9/0036 |
| WO | 2014/048562 A2 | 4/2014 | | |
| WO | 2014142133 A1 | 9/2014 | | |
| WO | 2016/102129 A1 | 6/2016 | | |

OTHER PUBLICATIONS

Beaumont Catherine et al, Water-Processable Self-Doped Conducting Polymers via Direct (Hetero)arylation Polymerization, Macromolecules, vol. 54, No. 12, Jun. 22, 2021 (Jun. 22, 2021), pp. 5464-5472, XP055865036, US ISSN: 0024-9297, DOI: 10.1021/acs.macromol. 1 c00847.

Stéphan et al., Electrochemical behavior of 3,4-ethylenedioxythiophene functionalized by a sulfonate group. Application to the preparation of poly(3,4-ethylenedioxythiophene) having permanent cation-exchange properties, Journal of Electroanalytical Chemistry, vol. 443, Issue 2, pp. 217-226 (1998), Feb. 20, 1998, Elsevier.

Office Action issued Apr. 30, 2025 in JP Application No. 2024517023.

Office Action issued Sep. 2, 2025 in JP Application No. 2024517023.

Office Action and Search Report issued Feb. 14, 2026 in CN Application No. 202280060127.5, with English translation of the Office Action.

* cited by examiner

PROCESS FOR PRODUCING
FUNCTIONALIZED POLYTHIOPHENES

The present invention relates to a process for producing a liquid composition comprising functionalized π-conjugated polythiophenes, to a liquid composition obtainable by this process, to a liquid composition comprising a functionalized π-conjugated polythiophene, wherein the composition, after is has been dried, is characterized by a certain weight loss at a given minimum temperature, to a process for the preparation of a layered body in which these liquid compositions are used for the formation of a conductive layer, to a layered body obtainable by this process and to the use of the liquid compositions for the preparation of a conductive layer in an electronic device.

A commercially available electrolyte capacitor as a rule is made of a porous metal electrode, an oxide layer serving as a dielectric on the metal surface, an electrically conductive material, usually a solid, which is introduced into the porous structure, an outer electrode (contacting), such as e.g. a silver layer, and further electrical contacts and an encapsulation. An electrolyte capacitor which is frequently used is the tantalum electrolytic capacitor, the anode electrode of which is made of the valve metal tantalum, on which a uniform, dielectric layer of tantalum pentoxide has been generated by anodic oxidation (also called "formation"). A liquid or solid electrolyte forms the cathode of the capacitor. Aluminium capacitors in which the anode electrode is made of the valve metal aluminium, on which a uniform, electrically insulating aluminium oxide layer is generated as the dielectric by anodic oxidation, are furthermore frequently employed. Here also, a liquid electrolyte or a solid electrolyte forms the cathode of the capacitor. The aluminium capacitors are usually constructed as wound- or stacked-type capacitors.

π-conjugated polymers are particularly suitable as solid electrolytes in the capacitors described above because of their high electrical conductivity. π-conjugated polymers are also called conductive polymers or synthetic metals. They are increasingly gaining economic importance, since polymers have advantages over metals with respect to processability, weight and targeted adjustment of properties by chemical modification. Examples of known π-conjugated polymers are polypyrroles, polythiophenes, polyanilines, polyacetylenes, polyphenylenes and poly (p-phenylene-vinylenes), a particularly important polythiophene used industrially being poly(3,4-ethylenedioxythiophene) (PEDOT), since it has a very high conductivity in its oxidized form.

The solid electrolytes based on conductive polymers can be applied to the oxide layer in various ways. EP-A-0 340 512 describes, for example, the production of a solid electrolyte from 3,4-ethylenedioxythiophene and the use thereof in electrolytic capacitors. According to the teaching of this publication, 3,4-ethylenedioxythiophene is polymerized on to the oxide layer in situ. In addition to the in situ polymerization a processes for the production of solid electrolytes in capacitors in which a dispersion comprising the already polymerized thiophene and a polyanion as a counter-ion, for example the PEDOT/PSS-dispersions (PEDOT=Poly(3,4-ethylenedioxythiophene; PSS=polystyrene sulfonic acid) known from the prior art, is applied to the oxide layer and the dispersing agent is then removed by evaporation are also known from the prior art. Such a process for the production of solid electrolyte capacitors is disclosed, for example, in DE-A-10 2005 043 828.

However, PEDOT/PSS-dispersion are characterized by the disadvantage that they comprise a significant amount of PSS as a non-conducting inert material. Furthermore, due to the presence of PSS the size of the PEDOT/PSS-particles in the dispersions is sometimes too large to ensure that the particles also penetrate into the smaller pores of the porous metal electrode. Finally, the maximum solids content of PEDOT/PSS-dispersions is often limited to values of about 3 wt.-%. In order to overcome these disadvantages, liquid compositions comprising derivatives of PEDOT have been prepared which are not characterized by the disadvantages of the known PEDOT/PSS-dispersions. Polythiophenes functionalized with sulfonate groups were developed initially. Due to the sulfonate groups, these polythiophenes are self-doped and do not require counter-ions such as PSS. EP 1 122 274 A1, for example, discloses the preparation of functionalized π-conjugated polymers such as poly(4-(2,3-dihydrothieno[3,4-b][1,4]dioxin-2-yl-methoxy)-1-butane-sulfonic acid) (PEDOT-S) by oxidative polymerization of the corresponding monomer 4-(2,3-dihydrothieno[3,4-b][1,4]dioxin-2-ylmethoxy)-1-butanesulfonic acid (EDOT-S). However, the electrical conductivity of conductive layers prepared by the polymer solutions obtained in EP 1 122 274 A1 are usually too low to use these polymer solutions for the preparation of, for example, a solid electrolyte layer in a solid electrolyte capacitor. Functionalized π-conjugated polymers such as PEDOT-S having a significantly increased electrical conductivity and a process for their preparation are disclosed in WO 2016/102129 A1.

Conductive polymers used to produce conductive layers in electronic components, such a solid electrolyte layers in capacitors, should not only be characterized by a sufficiently high conductivity, but also by high thermal stability. The reason for this is that high thermal stresses occur, for example during the soldering of the capacitors or in the subsequent use of electronic components, for example in the automotive industry.

It was therefore an object of the present invention to overcome the disadvantages of the prior art in the field of π-conjugated polymers.

In particular, it was an object of the present invention to provide compositions comprising a π-conjugated conductive polymer, preferably a water-soluble or water-dispersible π-conjugated conductive polymer, that, compared to the corresponding compositions known from the prior art, are characterized in that they not only display a high conductivity, but also an increased thermal stability of the π-conjugated conductive polymer. The term "thermal stability" as used herein preferably characterizes the ability of a conductive polymer to withstand a weight loss as a consequence of a thermal decomposition.

It was also an object of the present invention to provide compositions comprising a π-conjugated conductive polymer, preferably a water-soluble or water-dispersible π-conjugated conductive polymer, that, when used for the formation of a solid electrolyte layer in a capacitor, leads to advantageous properties of the capacitor, in particular to increased thermal stability compared to a capacitor the solid electrolyte layer of which has been prepared using the corresponding compositions known from the prior art.

A contribution to the solution of at least one of the above objects is provided by the subject matter of the category-forming independent claims, wherein the therefrom dependent sub-claims represent preferred embodiments of the present invention, whose subject matter likewise make a contribution to solving at least one object.

|1a| A contribution to solving at least one of the objects according to the invention is made by a 1<sup>st</sup> embodiment of process 1 of producing a liquid composition com-

3 prising functionalized π-conjugated polythiophenes, the process comprising the steps of i) providing a liquid phase comprising a functionalized π-conjugated polythiophene that is dissolved or dispersed in a solvent, wherein the functionalized π-conjugated polythiophene comprises repeating units of the general formula (I)

(I)

wherein
 X, Y are identical or different and are O, S, or $NR^1$, wherein $R^1$ is hydrogen or an aliphatic or aromatic residue having 1 to 18 carbon atoms;
 A is an organic residue carrying an anionic functional group;
 and wherein the liquid phase has a pH-value of less than 2.5, preferably less than 2.0;

ii) adjusting the pH-value of the liquid phase provided in process step i) to a value in the range from 2.5 to 10, preferably in the range from 3 to 8, by the addition of a base.

|2a| In a preferred embodiment of process 1 according to the present invention in the general formula (I)
 X, Y are O,
 A is $-(CR^2_2)_m-CR^2R^3-(CR^2_2)_n-$,
 wherein
 residues $R^2$ are independently from each other hydrogen or $-(CH_2)_s-Z-(CR^4_2)_p-SO_3^-M^+$,
 $R^3$ is $-(CH_2)_s-Z-(CR^4)_p-SO_3^-M^+$,
 Z is O, S or $-CH_2-$,
 $R^4$ is a hydrogen or an alkyl group;
 $M^+$ is a cation,
 m and n are identical or different and are an integer from 0 to 3,
 s is an integer from 0 to 10 and
 p is an integer from 1 to 18.

The term "residues $R^2$ are independently from each other hydrogen or $-(CH_2)_s-Z-(CR^4_2)_p-SO_3^-M^+$" indicates that at a given carbon atom both residues $R^2$ can be a hydrogen, both residues $R^2$ can be $-(CH_2)_s-Z-(CR^4_2)_p-SO_3^-M^-$ or one residue $R^2$ can be a hydrogen and one residue $R^2$ can be $-(CH_2)_s-Z-(CR^4_2)_p-SO_3^-M^+$. Moreover, in a given functionalized π-conjugated polythiophene residues $-(CH_2)_s-Z-(CR^4_2)_p-SO_3^-M^-$ do not necessarily have to be identical.

This preferred embodiment is a $2^{nd}$ embodiment of process 1 according to the present invention, that preferably depends on the $1^{st}$ embodiment.

|3a| In a further preferred embodiment of process 1 according to the present invention in the general formula (I)
 X, Y are O,
 A is $-(CH_2)_s-CR^2R^3-(CH_2)_n-$,
 wherein
 $R^2$ is hydrogen,
 $R^3$ is $-(CH_2)-O-(CH_2)_p-SO_3^-M^+$,
 $M^+$ is an inorganic cation, preferably $Na^+$ or $K^+$,
 n is 0 or 1,
 s is 0 or 1, and
 p is 4 or 5.

4

This preferred embodiment is a $3^{rd}$ embodiment of process 1 according to the present invention, that preferably depends on the $2^{nd}$ embodiment.

|4a| In a further preferred embodiment of process 1 according to the present invention in the general formula (I)
 X, Y are O,
 A is $-(CH_2)_s-CR^2R^3-(CH_2)_n-$,
 wherein
 $R^2$ is hydrogen,
 $R^3$ is $-(CH_2)_s-O-CH_2-CH_2-CHR^4-SO_3^-M^+$,
 $M^+$ is an inorganic cation, preferably $Na^+$ or $K^+$,
 $R^4$ is $CH_3$ or $CH_2CH_3$, preferably $CH_3$,
 n is 0 or 1,
 s is 0 or 1, and
 p is 4 or 5.

This preferred embodiment is a $4^{th}$ embodiment of process 1 according to the present invention, that preferably depends on the $2^{nd}$ embodiment.

|5a| In a further preferred embodiment of process 1 according to the present invention the π-conjugated polythiophene is poly(4-(2,3-dihydrothieno[3,4-b][1,4]dioxin-2-ylmethoxy)-1-butanesulfonic acid) or a salt thereof, poly(4-(2,3-dihydrothieno[3,4-b][1,4]dioxin-2-ylmethoxy)-2-butanesulfonic acid) or a salt thereof or a mixture of at these polymers. This preferred embodiment is a $5^{th}$ embodiment of process 1 according to the present invention, that preferably depends on anyone to the $1^{st}$ to the $4^{th}$ embodiment.

|6a| In a further preferred embodiment of process 1 according to the present invention the solvent is selected from the group consisting of water, aliphatic alcohols, such as methanol, ethanol, isopropanol and butanol, diacetone alcohols, ethylene glycol and glycerol, aliphatic ketones, such as acetone and methyl ethyl ketone, aliphatic nitrites, such as acetonitrile, glycol ethers, such polyethylene glycol methyl ether, and a mixture of at least two of these solvents, in particular a mixture of water and a water-miscible solvent, wherein the use of water as je solvent is most preferred. This preferred embodiment is a $6^{th}$ embodiment of process 1 according to the present invention, that preferably depends on anyone to the $1^{st}$ to the $5^{th}$ embodiment.

|7a| In a further preferred embodiment of process 1 according to the present invention the base is an inorganic base such as an alkali metal hydroxide or an earth alkali metal hydroxide, more preferably an inorganic base selected from the group consisting of ammonia, lithium hydroxide, lithium oxide, sodium hydroxide, sodium oxide, potassium hydroxide, potassium oxide, calcium hydroxide, calcium oxide, magnesium hydroxide, magnesium oxide, barium hydroxide, barium oxide, lithium silicate, sodium silicate, potassium silicate, lithium borate, sodium borate, potassium borate, lithium carbonate, sodium carbonate, potassium carbonate, lithium bicarbonate, sodium bicarbonate, potassium bicarbonate, trisodium phosphate and a mixture of at least two of these bases. This preferred embodiment is an $7^{th}$ embodiment of process 1 according to the present invention, that preferably depends on anyone to the $1^{st}$ to the $6^{th}$ embodiment.

|8a| In a further preferred embodiment of process 1 according to the present invention the base is an alkali metal hydroxide, preferably an alkali metal hydroxide selected from the group consisting of lithium hydroxide, sodium hydroxide, potassium hydroxide and a mixture of at least two of these bases. This preferred embodiment is an 8$^{th}$ embodiment of process 1 according to the present invention, that preferably depends on the 7$^{th}$ embodiment.

|9a| In a further preferred embodiment of process 1 according to the present invention the liquid phase provided in process step i) comprises the functionalized π-conjugated polythiophene in an amount in the range from 0.1 to 25 wt.-%, preferably in the range from 0.25 to 10 wt.-% and most preferably in the range from 0.5 to 4 wt.-%, in each case based on the total weight of the liquid phase. This preferred embodiment is a 9$^{th}$ embodiment of process 1 according to the present invention, that preferably depends on anyone of the 1$^{st}$ to the 8$^{th}$ embodiment.

|10a| In a further preferred embodiment of process 1 according to the present invention the functionalized π-conjugated polythiophene in the liquid phase provided in process step i) is characterized by a ratio of the mass average molecular weight M$_w$ to the molar average molecular weight M$_n$ (M$_w$/M$_n$) of at least 6, preferably at least 8, more preferably at least 10, more preferably at least 12, more preferably at least 14, more preferably at least 16, more preferably at least 18 and more preferably at least 20. This preferred embodiment is a 10$^{th}$ embodiment of process 1 according to the present invention, that preferably depends on anyone of the 1$^{st}$ to the 9$^{th}$ embodiment.

|11a| In a further preferred embodiment of process 1 according to the present invention the functionalized π-conjugated polythiophene in the liquid phase provided in process step i) is characterized by a mass average molecular weight M$_w$ of at least 50000 g/mol, preferably at least 75000 g/mol, more preferably at least 100000 g/mol and most preferably at least 125000 g/mol. This preferred embodiment is an 11$^{th}$ embodiment of process 1 according to the present invention, that preferably depends on the 10$^{th}$ embodiment.

|12a| In a further preferred embodiment of process 1 according to the present invention the functionalized π-conjugated polythiophene in the liquid phase provided in process step i) is characterized by a mass average molecular weight M$_w$ is in the range from 125000 g/mol to 240000 g/mol and preferably in the range from 125000 g/mol to 210000 g/mol. This preferred embodiment is a 12$^{th}$ embodiment of process 1 according to the present invention, that preferably depends on the 10$^{th}$ or the 11$^{th}$ embodiment.

|13a| In a further preferred embodiment of process 1 according to the present invention the functionalized π-conjugated polythiophene in the liquid phase provided in process step i) is characterized by a molar average molecular weight M$_n$ of less than 25000 g/mol, preferably less than 20000 g/mol and more preferably less than 15000 g/mol. This preferred embodiment is a 13$^{th}$ embodiment of process 1 according to the present invention, that preferably depends on anyone of the 10$^{th}$ to the 12$^{th}$ embodiment.

|14a| In a further preferred embodiment of process 1 according to the present invention the provision of the liquid phase in process step i) comprises the process steps of ia) providing a liquid reaction mixture comprising
  a) thiophene monomers of the general formula (I)

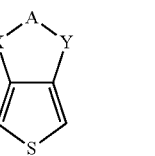

(I)

wherein X, Y and A are defined as defined above;
  b) an oxidizing agent; and
  c) a solvent;

ib) oxidatively polymerizing the thiophene monomers of the general formula (I) in the liquid reaction mixture obtained in process step ia) to obtain a liquid phase comprising a functionalized π-conjugated polythiophene;

ic) optionally purification of the liquid phase obtained in process step ib), preferably by means of ion filtration.

This preferred embodiment is a 14$^{th}$ embodiment of process 1 according to the present invention, that preferably depends on anyone of the 1$^{st}$ to the 13$^{th}$ embodiment.

|15a| In a preferred embodiment of the 14$^{th}$ embodiment of process 1 according to the present invention the pH of the liquid reaction mixture provided in process step ia) is adjusted to a value of less than 2.5 using an organic or inorganic acid, preferably an acid selected from the group consisting of formic acid, acetic acid, lactic acid, propionic acid, citric acid, malic acid, fumaric acid, sulfuric acid, sulfonic acid, nitric acid, phosphonic acid, phosphoric acid or a mixture of at least two of these acids, wherein the use of sulfuric acid is particularly preferred. This preferred embodiment is a 15$^{th}$ embodiment of process 1 according to the present invention, that preferably depends on the 14$^{th}$ embodiment.

|16a| In a further preferred embodiment of the 14$^{th}$ embodiment of process 1 according to the present invention the oxidative polymerization in process step ib) is performed under an inert gas atmosphere of nitrogen, argon, carbon dioxide or a mixture thereof. This preferred embodiment is a 16$^{th}$ embodiment of process 1 according to the present invention, that preferably depends on the 14$^{th}$ or the 15$^{th}$ embodiment.

|17a| In a further preferred embodiment of the 14$^{th}$ embodiment of process 1 according to the present invention the oxidative polymerization in process step ib) is performed under a pressure that is equal to or above the vapor pressure of the liquid reaction mixture during the polymerization reaction in process step ib). This preferred embodiment is a 17$^{th}$ embodiment of process 1 according to the present invention, that preferably depends on anyone of the 14$^{th}$ to the 16$^{th}$ embodiment.

|18a| In a further preferred embodiment of the 14$^{th}$ embodiment of process 1 according to the present invention the oxidative polymerization in process step ib) is performed under a reduced pressure of not more than 0.8 bar. This preferred embodiment is an 18$^{th}$ embodiment of process 1 according to the present invention, that preferably depends on anyone of the 14$^{th}$ to the 17$^{th}$ embodiment.

|19a| In a further preferred embodiment of the 14$^{th}$ embodiment of process 1 according to the present invention the liquid phase obtained in process step ib) is purified in a further process step ic). This preferred embodiment is a 19$^{th}$ embodiment of process 1 accord-

7

8 ing to the present invention, that preferably depends on anyone of the 14$^{th}$ to the 18$^{th}$ embodiment.

|20a| In a further preferred embodiment of the 14$^{th}$ embodiment of process 1 according to the present invention purification in process step ic) is accomplished by means of filtration and/or by means of a treatment with ion exchanger. This preferred embodiment is a 20$^{th}$ embodiment of process 1 according to the present invention, that preferably depends on the 19$^{th}$ embodiment.

|21a| In a further preferred embodiment of process 1 according to the present invention, the liquid phase provided in process step i) comprises further additives, preferably further additives selected from the group consisting of surface-active substances, adhesion promoters, additives which increase the conductivity, organic binders or mixtures of at least two of these further additives. This preferred embodiment is a 21$^{st}$ embodiment of process 1 according to the present invention, that preferably depends on anyone of the 1$^{st}$ to the 20$^{th}$ embodiment.

|1b| A contribution to solving at least one of the objects according to the invention is also made by a 1$^{st}$ embodiment of liquid composition 1 comprising functionalized π-conjugated polythiophenes obtainable by process 1 according to the present invention, preferably by process 1 according to anyone of the 1$^{st}$ to the 20$^{th}$ embodiment.

|2b| In a preferred embodiment of the liquid composition 1 according to the present invention a composition that is obtained after drying the liquid composition 1 at a temperature of 100° C. and a pressure of 50 mbar for 16 hours, fulfills at least one of the following conditions (A) to (E):

(A) a weight loss of 10 wt.-%, based on the total weight of the dried liquid composition, at a temperature of not less than 300° C., preferably of not less than 310° C. and even more preferably of not less than 320° C. as determined by means of thermogravimetric analysis;

(B) a weight loss of 20 wt.-%, based on the total weight of the dried liquid composition, at a temperature of not less than 330° C., preferably of not less than 335° C. and even more preferably of not less than 340° C. as determined by means of thermogravimetric analysis;

(C) a weight loss of 30 wt.-%, based on the total weight of the dried liquid composition, at a temperature of not less than 345° C., preferably of not less than 350° C. and even more preferably of not less than 355° C. as determined by means of thermogravimetric analysis;

(D) absence of a peak in the derivative plot in the interval between 250° C. and 270° C.;

(E) a ratio of the derivative value at 261° C. to the derivative value at the 2$^{nd}$ peak of 0.1 or less, preferably of 0.08 or less and more preferably of 0.07 or less.

This preferred embodiment is a 2$^{nd}$ embodiment of liquid composition 1 according to the present invention, that preferably depends on the 1$^{st}$ embodiment. In this context it is particularly preferred, that the dried liquid composition 1 fulfils the following condition or combination of conditions: A, B, C, D, E, AB, AC, AD, AE, BC, BD, BE, CD, CE, DE, ABC, ABD, ABE, ACD, ACE, ADE, BCD, BCE, BDE, CDE, ABCD, ABCE, ABDE, ACDE, BCDE and ABCDE.

|3b| In a further preferred embodiment of liquid composition 1 according to the present invention a conductive layer made by the liquid composition has a conductivity of more than 25 S/cm. This preferred embodiment is a 3$^{rd}$ embodiment of liquid composition 1 according to the present invention, that preferably depends on the 1$^{st}$ or the 2$^{nd}$ embodiment.

|4b| In a further preferred embodiment of liquid composition 1 according to the present invention the liquid composition comprises further additives, preferably further additives selected from the group consisting of surface-active substances, adhesion promoters, additives which increase the conductivity, organic binders or mixtures of at least two of these further additives. This preferred embodiment is a 4$^{th}$ embodiment of liquid composition 1 according to the present invention, that preferably depends on anyone of the 1$^{st}$ to the 3$^{rd}$ embodiment.

|1c| A contribution to solving at least one of the objects according to the invention is also made by a 1$^{st}$ embodiment of liquid composition 2 having a pH-value in the range from 2.5 to 10, preferably in the range from 3 to 8, and comprising a functionalized π-conjugated polythiophene that is dissolved or dispersed in a solvent, wherein the polythiophene comprises repeating units of the general formula (I)

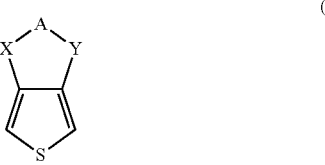

(I)

wherein

X, Y are identical or different and are O, S, or NR$^1$, wherein R$^1$ is hydrogen or an aliphatic or aromatic residue having 1 to 18 carbon atoms;

A is an organic residue carrying an anionic functional group;

wherein a composition that is obtained after drying the liquid composition 2 at a temperature of 100° C. and a pressure of 50 mbar for 16 hours, fulfills at least one of the following conditions (A) to (E):

(A) a weight loss of 10 wt.-%, based on the total weight of the dried liquid composition, at a temperature of not less than 300° C., preferably of not less than 310° C. and even more preferably of not less than 320° C. as determined by means of thermogravimetric analysis;

(B) a weight loss of 20 wt.-%, based on the total weight of the dried liquid composition, at a temperature of not less than 330° C., preferably of not less than 335° C. and even more preferably of not less than 340° C. as determined by means of thermogravimetric analysis;

(C) a weight loss of 30 wt.-%, based on the total weight of the dried liquid composition, at a temperature of not less than 345° C., preferably of not less than 350° C. and even more preferably of not less than 355° C. as determined by means of thermogravimetric analysis;

(D) absence of a peak in the derivative plot in the interval between 250° C. and 270° C.;

(E) a ratio of the derivative value at 261° C. to the derivative value at the 2$^{nd}$ peak of 0.1 or less, preferably of 0.08 or less and more preferably of 0.07 or less.

In this context it is particularly preferred, that the dried liquid composition 2 fulfils the following condition or combination of conditions: A, B, C, D, E, AB, AC, AD, AE, BC, BD, BE, CD, CE, DE, ABC, ABD, ABE, ACD, ACE, ADE, BCD, BCE, BDE, CDE, ABCD, ABCE, ABDE, ACDE, BCDE and ABCDE.

|2c| In a preferred embodiment of liquid composition 2 according to the present invention in the general formula (I)

X, Y are O,

A is —$(CR^2{}_2)_m$—$CR^2R^3$—$(CR^2{}_2)_n$—, wherein residues $R^2$ are independently from each other hydrogen or —$(CH_2)_s$—Z—$(CR^4{}_2)_p$—$SO_3^-M^+$, $R^3$ is —$(CH_2)_s$—Z—$(CR^4)_p$—$SO_3^-M^+$, Z is O, S or —$CH_2$—, $R^4$ is a hydrogen or an alkyl group;

$M^+$ is a cation, m and n are identical or different and are an integer from 0 to 3, s is an integer from 0 to 10 and p is an integer from 1 to 18.

This preferred embodiment is a $2^{nd}$ embodiment of liquid composition 2 according to the present invention, that preferably depends on the $1^{st}$ embodiment.

|3c| In a further preferred embodiment of liquid composition 2 according to the present invention in the general formula (I)

X, Y are O,

A is —$(CH_2)_s$—$CR^2R^3$—$(CH_2)_n$—, wherein $R^2$ is hydrogen, $R^3$ is —$(CH_2)$—O—$(CH_2)_p$—$SO_3^-M^+$, $M^+$ is an inorganic cation, preferably $Na^+$ or $K^+$, n is 0 or 1, s is 0 or 1, and p is 4 or 5.

This preferred embodiment is a $3^{rd}$ embodiment of liquid composition 2 according to the present invention, that preferably depends on the $2^{nd}$ embodiment.

|4c| In a further preferred embodiment of liquid composition 2 according to the present invention in the general formula (I)

X, Y are O,

A is —$(CH_2)_s$—$CR^2R^3$—$(CH_2)_n$—, wherein $R^2$ is hydrogen, $R^3$ is —$(CH_2)_s$—O—$CH_2$—$CH_2$—$CHR^4$—$SO_3^-M^+$, $M^+$ is an inorganic cation, preferably $Na^+$ or $K^+$, $R^4$ is $CH_3$ or $CH_2CH_3$, preferably $CH_3$, n is 0 or 1, s is 0 or 1, and p is 4 or 5.

This preferred embodiment is a $4^{th}$ embodiment of liquid composition 2 according to the present invention, that preferably depends on the $2^{nd}$ embodiment.

|5c| In further preferred embodiment of liquid composition 2 according to the present invention the π-conjugated polythiophene is poly(4-(2,3-dihydrothieno[3,4-b][1,4]dioxin-2-yl-methoxy)-1-butanesulfonic acid) or a salt thereof, poly(4-(2,3-dihydrothieno[3,4-b][1,4]dioxin-2-ylmethoxy)-2-butanesulfonic acid) or a salt thereof or a mixture of at these polymers. This preferred embodiment is a $5^{th}$ embodiment of liquid composition 2 according to the present invention, that preferably depends on anyone to the $1^{st}$ to the $4^{th}$ embodiment.

|6c| In a further preferred embodiment of liquid composition 2 according to the present invention the solvent is selected from the group consisting of water, aliphatic alcohols, such as methanol, ethanol, isopropanol and butanol, diacetone alcohols, ethylene glycol and glycerol, aliphatic ketones, such as acetone and methyl ethyl ketone, aliphatic nitrites, such as acetonitrile, glycol ethers, such polyethylene glycol methyl ether, and a mixture of at least two of these solvents, in particular a mixture of water and a water-miscible solvent, wherein water is most preferred as the solvent. This preferred embodiment is a $6^{th}$ embodiment of liquid composition 2 according to the present invention, that preferably depends on anyone to the $1^{st}$ to the $5^{th}$ embodiment.

|7c| In a further preferred embodiment of liquid composition 2 according to the present invention the liquid composition comprises the functionalized π-conjugated polythiophene in an amount in the range from 0.1 to 25 wt.-%, preferably in the range from 0.25 to 10 wt.-% and most preferably in the range from 0.5 to 4 wt.-%, in each case based on the total weight of liquid composition 2. This preferred embodiment is a $7^{th}$ embodiment of liquid composition 2 according to the present invention, that preferably depends on anyone of the $1^{st}$ to the $6^{th}$ embodiment.

|8c| In a further preferred embodiment of liquid composition 2 according to the present invention the functionalized π-conjugated polythiophene is present in the form of particles, wherein the particle size distribution of these particles is characterized by i) a $d_{50}$-value (weight average particle diameter) in the range from 1 to 100 nm, preferably in the range from 1 to 80 nm, more preferably in the range from 1 to 60 nm and most preferable in the range from 5 to 40 nm, and ii) a $d_{90}$-value of less than $3.5 \times d_{50}$, preferably less than $3 \times d_{50}$ and more preferably less than $2 \times d_{50}$.

This preferred embodiment is an $8^{th}$ embodiment of liquid composition 2 according to the present invention, that preferably depends on anyone of the $1^{st}$ to the $7^{th}$ embodiment.

|9c| In a further preferred embodiment of liquid composition 2 according to the present invention the functionalized π-conjugated polythiophene in the liquid composition is characterized by a ratio of the mass average molecular weight $M_w$ to the molar average molecular weight $M_n$ ($M_w/M_n$) of at least 6, preferably at least 8, more preferably at least 10, more preferably at least 12, more preferably at least 14, more preferably at least 16, more preferably at least 18 and more preferably at least 20. This preferred embodiment is a $9^{th}$ embodiment of liquid composition 2 according to the present invention, that preferably depends on anyone of the $1^{st}$ to the $8^{th}$ embodiment.

|10c| In a further preferred embodiment of liquid composition 2 according to the present invention the functionalized π-conjugated polythiophene in the liquid composition is characterized by a mass average molecular weight $M_w$ of at least 50000 g/mol, preferably at least 75000 g/mol, more preferably at least 100000 g/mol and most preferably at least 125000 g/mol.

This preferred embodiment is a $10^{th}$ embodiment of liquid composition 2 according to the present invention, that preferably depends on the $9^{th}$ embodiment.

|11c| In a further preferred embodiment of liquid composition 2 according to the present invention the functionalized π-conjugated polythiophene in the liquid composition is characterized by a mass average molecular weight $M_w$ is in the range from 125000 g/mol to 240000 g/mol and preferably in the range from 125000 g/mol to 210000 g/mol. This preferred embodiment is an $11^{th}$ embodiment of liquid composition 2 according to the present invention, that preferably depends on the $9^{th}$ or the $10^{th}$ embodiment.

|12c| In a further preferred embodiment of liquid composition 2 according to the present invention the functionalized π-conjugated polythiophene in the liquid composition is characterized by a molar average molecular weight $M_n$ of less than 25000 g/mol, preferably less than 20000 g/mol and more preferably less than 15000 g/mol. This preferred embodiment is a $12^{th}$ embodiment of liquid composition 2 according to the present invention, that preferably depends on anyone of the $9^{th}$ to the $11^{th}$ embodiment.

|13c| In a further preferred embodiment of liquid composition 2 according to the present invention a conductive layer made by the liquid composition has a conductivity of more than 25 S/cm. This preferred embodiment is a $13^{th}$ embodiment of liquid composition 2 according to the present invention, that preferably depends on anyone of the $1^{st}$ to the $12^{th}$ embodiment.

|14c| In a further preferred embodiment of liquid composition 2 according to the present invention the liquid composition comprises further additives, preferably further additives selected from the group consisting of surface-active substances, adhesion promoters, additives which increase the conductivity, organic binders or mixtures of at least two of these further additives. This preferred embodiment is a $14^{th}$ embodiment of liquid composition 2 according to the present invention, that preferably depends on anyone of the $1^{st}$ to the $13^{th}$ embodiment.

|1d| A contribution to solving at least one of the objects according to the invention is also made by process 2 for the preparation of a layered body, comprising the process steps:

I) provision of a substrate;

II) application of the liquid composition 1 or a liquid composition 2 according to the present invention, preferably of a liquid composition 1 according to anyone of its $1^{st}$ to the $4^{th}$ embodiment or of a liquid composition 2 according to anyone of its $1^{st}$ to the $14^{th}$ embodiment, to at least a part of at least one surface of the substrate;

III) optionally at least partial removal of the solvent for the formation of a conductive layer that covers at least a part of at least one surface of the substrate

|2d| In a preferred embodiment of process 2 according to the present invention the substrate is an electrode body of an electrode material, wherein a dielectric covers one surface of this electrode material at least partly under formation of an anode body. This preferred embodiment is a $2^{nd}$ embodiment of process 2 according to the present invention, that preferably depends on the $1^{st}$ embodiment.

|1e| A contribution to solving at least one of the objects according to the invention is also made by a layered body, obtainable by process 2 according to the present invention, preferably by process 2 according to the $1^{st}$ or the $2^{nd}$ embodiment.

|1f| A contribution to solving at least one of the objects according to the invention is also made by the use of the liquid composition 1 or a liquid composition 2 according to the present invention, preferably of a liquid composition 1 according to anyone of its $1^{st}$ to the $4^{th}$ embodiments or a liquid composition 2 according to anyone of its $1^{st}$ to the $14^{th}$ embodiment, for the preparation of a conductive layer in an electronic device.

|2f| In a preferred embodiment of the use according to the present invention the electronic device is selected from photoconductive cells, photoresistors, photoswitches, phototransistors, phototubes, IR detectors, photovoltaic device, solar cells, coating materials for memory storage devices, field effect resistance devices, antistatic films, biosensors, electrochromic devices, electrolyte capacitors, energy storage devices, touch panels and electromagnetic shielding. This preferred embodiment is a $2^{nd}$ embodiment of the use according to the present invention, that preferably depends on the $1^{st}$ embodiment.

|3f| In a further preferred embodiment of the use according to the present invention the conductive layer is a solid electrolyte layer in a polymer electrolyte capacitor or hybrid electrolyte capacitor. This preferred embodiment is a $3^{rd}$ embodiment of the use according to the present invention, that preferably depends on the $1^{st}$ or the $2^{nd}$ embodiment.

Process 1 According to the Invention

A contribution towards solving these objects is made by process 1 for producing a liquid composition comprising functionalized π-conjugated polythiophenes, the process comprising the steps of i) providing a liquid phase comprising a functionalized π-conjugated polythiophene that is dissolved or dispersed in a solvent, wherein the functionalized π-conjugated polythiophene comprises repeating units of the general formula (I)

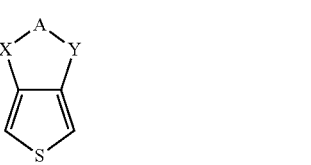

(I)

wherein

X, Y are identical or different and are O, S, or $NR^1$, wherein $R^1$ is hydrogen or an aliphatic or aromatic residue having 1 to 18 carbon atoms;

A is an organic residue carrying an anionic functional group;

and wherein the liquid phase has a pH-value of less than 2.5, preferably less than 2.0;

ii) adjusting the pH-value of the liquid phase provided in process step i) to a value in the range from 2.5 to 10, preferably in the range from 3 to 8, by the addition of a base.

Surprisingly it has been discovered that by adjusting the pH-value of a liquid composition comprising functionalized π-conjugated polythiophenes (such as PEDOT-S), having a pH of less than 2.5, to a value in the range from 2.5 to 10 by the addition of a base, preferably by the addition of an alkali metal hydroxide, functionalized π-conjugated polythiophenes are obtained that are characterized by a significantly increased thermal stability.

In the functionalized π-conjugated polythiophene that is comprised in the liquid phase provided in process step i) (or that is comprised in the liquid composition according to the present invention) repeating units of the general formula (I) are bonded to each other as shown in the following formula (I')

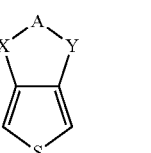

(I')

in which the asterisks (*) indicate the bond to the adjacent repeating units. Preferably, the functionalized π-conjugated polythiophene has positive charges along the polymer chain (not shown in formula (I')) and these positive charges are at least partly compensated by the anionic functional groups in organic residues A.

In process step i) of the process 1 according to the present invention a liquid phase is provided that comprises a functionalized π-conjugated polythiophene that is dissolved or dispersed in a solvent. Preferably, process step i) comprises the sub-steps of ia) providing a liquid reaction mixture comprising
        a) thiophene monomers of the general formula (I)

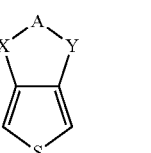

(I)

wherein X, Y and A are defined as defined above;
        b) an oxidizing agent; and
        c) a solvent;
    ib) oxidatively polymerizing the thiophene monomers of the general formula (I) in the liquid reaction mixture obtained in process step ia) to obtain a liquid phase comprising a functionalized π-conjugated polythiophene;
    ic) optionally purification of the liquid phase obtained in process step ib), preferably by means of ion filtration.

Among the preferred functionalized π-conjugated polythiophene to be uses in the process and the liquid compositions according to the present invention is poly(4-(2,3-dihydrothieno[3,4-b][1,4]dioxin-2-ylmethoxy)-1-butanesulfonic acid) or a salt thereof and one of the preferred thiophene monomer a) is therefore 4-(2,3-dihydrothieno[3,4-b][1,4]dioxin-2-ylmethoxy)-1-butanesulfonic acid. A further preferred functionalized π-conjugated polythiophene to be used in process and the liquid compositions according to the present invention is poly(4-(2-(2,3-dihydrothieno[3,4-b][1,4]dioxin-2-ylmethoxy)-2-butanesulfonic acid) or a salt thereof and a further preferred thiophene monomer a) is therefore 4-(2,3-dihydrothieno[3,4-b][1,4]dioxin-2-yl-methoxy)-2-butanesulfonic acid.

The oxidation reaction that is performed in process step ib) can be catalyzed by a chemical oxidizing agent, by electrochemical oxidation or by a combination of both methods. In case of an electrochemical oxidation an electrode functions as the oxidizing agent b).

Suitable oxidizing agents b) used as chemical oxidizing agents are salts of heavy metals, preferably iron salts, more preferably $FeCl_3$ and iron(III) salts of aromatic and aliphatic sulfonic acids, $H_2O_2$, $K_2Cr_2O_7$, salts of a salt of a peroxodisulfate, such as $K_2S_2O_8$, $Na_2S_2O_8$, $KMnO_4$, alkali metal perborates, and alkali metal or ammonium persulfates, or mixtures of these oxidants. Particularly preferred are salts of a heavy metal, salts of a peroxodisulfate or a mixture thereof. Further suitable oxidants are described, for example, in Handbook of Conducting Polymers (Ed. Skotheim, T. A.), Marcel Dekker: New York, 1986, Vol. 1, pages 46-57. Particularly preferred oxidizing agents b) are salts of a peroxodisulfate, in particular $K_2S_2O_8$, $Na_2S_2O_8$, iron salts, in particular iron(III) chloride, or mixtures of salts of a peroxodisulfate and at least one further compound that catalyzes the cleavage of the peroxodisulfate, like mixtures of salts of a peroxodisulfate and iron salts. According to a particularly preferred embodiment of the process according to the present invention the oxidizing agent is a mixture of $Fe_2(SO_4)_3$ and $Na_2S_2O_8$.

Suitable solvents c) that can be used in process 1 according to the present invention are water, water-miscible solvents, in particular those selected from the group consisting aliphatic alcohols, such as methanol, ethanol, isopropanol and butanol, diacetone alcohols, ethylene glycol and glycerol, aliphatic ketones, such as acetone and methyl ethyl ketone, aliphatic nitriles, such as acetonitrile, glycol ethers, such polyethylene glycol methyl ether, or a mixture of at least two of these solvents, in particular a mixture of water and a water-miscible solvent. The most preferred solvent, however, is water. In case of 4-(2,3-dihydrothieno[3,4-b][1,4]dioxin-2-yl-methoxy)-1-butanesulfonic acid or 4-(2,3-dihydrothieno[3,4-b][1,4]dioxin-2-ylmethoxy)-2-butanesulfonic acid as the thiophene monomer a) process 1 according to the present invention therefore enables the production of an aqueous solution comprising a functionalized π-conjugated polythiophene.

The concentration of the thiophene monomer a) in the liquid reaction mixture provided in process step ia) is preferably in a range from 0.1 to 40 wt.-%, preferably in a range from 5 to 15 wt.-%.

There are different ways of preparing the liquid reaction mixture provided in process step ia). The thiophene monomer a) can be dissolved or dispersed in the solvent c), followed by the addition of the oxidizing agent(s) b) (which can also be dissolved or dispersed in a solvent separately), or the oxidizing agent(s) b) is/are first dissolved or dispersed in the solvent c), followed by the addition of the thiophene monomer a) (which can also be dissolved or dispersed in a solvent separately). If more than one oxidizing agent is used, like a mixture of $Fe_2(SO_4)_3$ and $Na_2S_2O_8$, it is furthermore possible to first mix one of these components with the thiophene monomer a) and the solvent c) and to finally add the second oxidizing agent.

Irrespective the way in which the liquid reaction mixture is prepared in process step ia), it is particularly preferred to reduce the oxygen content in the components that are used to prepare the liquid reaction mixture to such an extent that the oxygen content in the liquid reaction mixture is below 1,000 ppm, more preferably less than 500 ppm, more preferably less than 100 ppm, more preferably less than 10 ppm, more preferably less than 1 ppm, more preferably less than 0.5 ppm and most preferably less than 0.25 ppm, in each case based on the total weight of the liquid reaction mixture. According to a particularly preferred embodiment of process 1 according to the present invention the components that are used to prepare the liquid reaction mixture are completely free of any oxygen (i.e. the oxygen content is 0 ppm).

The reduction of the oxygen content can, for example, be accomplished by stirring the components used to prepare the liquid reaction mixture under a reduced pressure, by using ultra sound or by degassing these components using an inert gas such as $N_2$, argon, $CO_2$ or a mixture thereof, or by a combination of the above-mentioned approaches.

The polymerization reaction in process step ib) is preferably performed at a temperature in the range from −20° C. to 200° C., preferably from 0° C. to 100° C. and for a duration of preferably 1 to 48 hours, more preferably for 5 to 20 hours.

After the polymerization reaction is completed, the liquid phase comprising the functionalized π-conjugated polymer, preferably the aqueous solution comprising the functionalized π-conjugated polymer, may be further purified, for example by means of filtration, in particular by means of ultrafiltration, and/or by a treatment with ion exchanger in a further process step ic), in particular by a treatment with an anion exchanger and a cation exchanger, for the purpose of further purification. It is also possible to add further additives as described below in connection with the process 2 according to the present invention.

Furthermore, as the functionalized π-conjugated polythiophenes obtained after polymerization in process step ib) is usually present in the form of particles, the particle size distribution of the functionalized π-conjugated polythiophenes in the liquid phase obtained in process step ib) or that—after further purification—is obtained in process step ic) can be adjusted by a treatment of the liquid phase with ultrasound, wherein the energy input is preferably between 10-1000 Watts/liter (W/l), more preferably between 20-500 W/l and the ultrasound frequency is preferably between 20-200 kHz, by a treatment of the liquid phase with high pressure homogenization, wherein pressures higher than 100 bar, preferably higher than 500 bar and most preferably higher than 1500 bar are applied preferably multiple times, or by a treatment of the liquid phase with heat, wherein the heat treatment preferably comprises a treatment of the liquid phase at a temperature in the range from 40 to 100° C., preferably at a range from 50 to 95° C. for a duration of 5 minutes to 100 hours, preferably 1 to 10 hours and more preferably 2 to 8 hours.

Process 1 according to the present invention is characterized in that the pH of the liquid phase provided in process step i) is less than 2.5. Such a pH can, for example, be obtained by adjusting the pH of the liquid rection mixture provided in process ia) to a value below 2.5, preferably below 2.0 and more preferably below 1.5, wherein the pH is determined at a temperature of 20° C.

Adjusting the pH-value to a value below 2.5 is preferably accomplished using an inorganic or organic acid, preferably an organic or inorganic acid that is substantially free of chloride. Suitable organic acids include carboxylic acids such as formic acid, acetic acid, lactic acid, propionic acid, citric acid, malic acid, fumaric acid or mixtures thereof. Suitable inorganic acids are in particular sulfuric acid, sulfonic acid, nitric acid, phosphonic acid, phosphoric acid or mixtures thereof. According to a particularly preferred embodiment of the process according to the present invention sulfuric acid is used for the adjustment of the pH.

According to a particularly preferred embodiment of process 1 according to the present invention it is also advantageous that the oxygen content of the liquid reaction mixture provided in process step ia) is less than 1,000 ppm, preferably less than 500 ppm, more preferably less than 100 ppm, more preferably less than 10 ppm, more preferably less than 1 ppm, more preferably less than 0.5 ppm and most preferably less than 0.25 ppm, in each case based on the total weight of the liquid reaction mixture. According to a particularly preferred embodiment of process 1 according to the present invention the oxygen content of the liquid reaction mixture provided in process step ia) is completely free of any oxygen (i.e. the oxygen content is 0 ppm).

There are different approaches of adjusting the oxygen content in the liquid reaction mixture that is provided in process step ia) and also to maintain this low oxygen content during the polymerization reaction in process step ib).

According to one approach the liquid reaction mixture provided in process step ia) (or the liquid components that are used to prepare the liquid reaction mixture) can be degassed, for example by introducing an inert gas such as $N_2$, Argon, $CO_2$ or a mixture thereof into the liquid phase provided in process step ia) to reduce the initial oxygen content in the liquid phase. Alternatively, the liquid reaction mixture provided in process step ia) (or the liquid components that are used to prepare the liquid reaction mixture) can be subjected to a treatment with a reduced pressure in order to reduce the initial oxygen content, for example by stirring the liquid reaction mixture while applying a vacuum, or can be subjected to a treatment with ultra sound or can be subjected to a combination of a treatment with a reduced pressure and a treatment with ultra sound.

In order to ensure that the low oxygen content is maintained during the polymerization reaction in process step ib) it may be advantageous to perform the polymerization reaction under an inert gas atmosphere, preferably under a $N_2$-atmosphere, under a $CO_2$-atmosphere, under an argon atmosphere or under an atmosphere of a mixture of at least two of these inert gases, wherein it may also be advantageous that the oxidative polymerization in process step ib) is performed under a pressure that is equal to or above the vapor pressure of the liquid reaction mixture during the polymerization reaction in process step ib). Preferably, the oxidative polymerization in process step ib) is performed under a pressure that is at least 0.1 mbar, more preferably at least 0.5 mbar and most preferably at least 1 mbar above the vapor pressure of the liquid reaction mixture during the polymerization reaction in process step ib). To ensure that the low oxygen content is maintained during the polymerization reaction in process step ib) it is also possible to perform the oxidative polymerization in process step ib) under a reduced pressure, preferably under a pressure of not more than 0.8 bar and most preferably under a pressure of not more than 0.5 bar.

In process step ii) of process 1 according to the present invention the pH-value of the liquid phase provided in process step i) is adjusted to a value in the range from 2.5 to 10, preferably in the range from 3 to 8, by the addition of a base, wherein the pH is again determined at a temperature of 20° C.

In this context it is particularly preferred that the base is an inorganic base, such as an alkali metal hydroxide or an earth alkali metal hydroxide, more preferably an inorganic base selected from the group consisting of ammonia, lithium hydroxide, lithium oxide, sodium hydroxide, sodium oxide, potassium hydroxide, potassium oxide, calcium hydroxide, calcium oxide, magnesium hydroxide, magnesium oxide, barium hydroxide, barium oxide, lithium silicate, sodium silicate, potassium silicate, lithium borate, sodium borate, potassium borate, lithium carbonate, sodium carbonate, potassium carbonate, lithium bicarbonate, sodium bicarbonate, potassium bicarbonate, trisodium phosphate and a mixture of at least two of these bases, wherein an alkali metal hydroxide, particularly an alkali metal hydroxide selected from the group consisting of lithium hydroxide, sodium hydroxide, potassium hydroxide and a mixture of at least two of these bases is most preferred as the base by means of which the pH is adjusted in process step ii).

Process 2 According to the Invention

A contribution towards achieving the abovementioned objects is also made by process 2 for the preparation of a layered body, comprising the process steps:

I) provision of a substrate;

II) application of the liquid composition 1 or a liquid composition 2 according to the present invention, preferably a liquid composition 1 according to anyone of its $1^{st}$ to the $5^{th}$ embodiment or a liquid composition 2 according to anyone of its $1^{st}$ to the $15^{th}$ embodiment, to at least a part of at least one surface of the substrate;

III) optionally at least partial removal of the solvent for the formation of a conductive layer that covers at least a part of at least one surface of the substrate.

According to a particularly preferred embodiment of process 2 according to the present invention the substrate is an electrode body of an electrode material, wherein a dielectric covers one surface of this electrode material at least partly under formation of an anode body. In such an embodiment process step II) thus comprises the process steps:

I) the provision of an electrode body of an electrode material, wherein a dielectric covers one surface of this electrode material at least partly under formation of an anode body;

II) the introduction of a liquid composition 1 or 2 according to the present invention, preferably a liquid composition 1 according to anyone of its $1^{st}$ to the $4^{th}$ embodiment or a liquid composition 2 according to anyone of its $1^{st}$ to the $14^{th}$ embodiment, into at least a part of the electrode body;

In process step I), an electrode body of an electrode material, wherein a dielectric covers one surface of this electrode material at least partly to form an anode body, is first provided.

In principle, the electrode body can be produced by pressing a valve metal powder of high surface area and sintering it to give a usually porous electrode body. An electrical contact wire, preferably of a valve metal, such as e.g., tantalum, is conventionally also pressed into the electrode body here. The electrode body is then coated, for example by electrochemical oxidation, with a dielectric, i.e., an oxide layer. Alternatively, metal foils can also be etched, and coated with a dielectric by electrochemical oxidation in order to obtain an anode foil having a porous region. In a wound capacitor, an anode foil having a porous region, which forms the electrode body, and a cathode foil are separated by separators and wound up.

In the context of the invention, valve metal is to be understood as meaning those metals of which the oxide layers do not render possible current flow equally in both directions. In the case of an anodically applied voltage, the oxide layers of the valve metals block the current flow, while in the case of a cathodically applied voltage large currents occur, which may destroy the oxide layer. The valve metals include Be, Mg, Al, Ge, Si, Sn, Sb, Bi, Ti, Zr, Hf, V, Nb, Ta and W and an alloy or compound of at least one of these metals with other elements. The best-known representatives of the valve metals are Al, Ta and Nb. Compounds which have electrical properties comparable to a valve metal are those having metallic conductivity, which can be oxidized and of which the oxide layers have the properties described above. For example, NbO has metallic conductivity, but in general is not regarded as a valve metal. Layers of oxidized NbO have, however, the typical properties of valve metal oxide layers, so that NbO or an alloy or compound of NbO with other elements are typical examples of such compounds which have electrical properties comparable to a valve metal. Electrode materials of tantalum, aluminium and those electrode materials based on niobium or niobium oxide are preferred. Tantalum and aluminium are very particularly preferred as the electrode material.

For production of the electrode body, often with a porous region, the valve metals can be sintered, for example in powder form, to give a usually porous electrode body, or a porous structure is stamped on a metallic body. The latter can be carried out e.g. by etching a foil.

For simplicity, bodies having a porous region are also called porous in the following. Thus, for example, electrode bodies having a porous region are also called porous electrode bodies. On the one hand, the porous bodies can be permeated by a plurality of channels and therefore be sponge-like. This is often the case if tantalum is used for construction of the capacitor. Furthermore, it is possible for only the surface to have pores and for the region following under the surface pores to be solid in construction. Such a situation is often observed if aluminium is used for construction of the capacitor. Preferably, the electrode body is porous.

The often-porous electrode bodies produced in this manner are then oxidized, for example, in a suitable electrolyte, such as e.g. phosphoric acid or an aqueous solution of ammonium adipate, by application of a voltage, in order to form the dielectric. The level of this formation voltage depends on the oxide layer thickness to be achieved or the later use voltage of the capacitor. Preferred formation voltages lie in a range of from 1 to 1000 V, particularly preferably in a range of from 2 to 500 V, very particularly preferably in a range of from 1 to 300 V. According to a first particular embodiment of the process for the production of a capacitor the formation voltage is in a range of from 1 to 20 V, whereas according to a second particular embodiment of the process for the production of a capacitor the formation voltage is in a range of from 30 to 100 V.

The as a rule porous electrode bodies employed preferably have a porosity of from 10 to 90%, preferably from 30 to 80%, particularly preferably from 50 to 80% and an average pore diameter of from 10 to 10000 nm, preferably from 20 to 5,000 nm, particularly preferably from 50 to 3000 nm.

According to a particular embodiment of process 2 according to the invention, the electrolyte capacitor to be produced is an aluminium wound capacitor. In this case, a porous aluminium foil is formed anodically as the electrode material, an aluminium oxide coating being formed as the dielectric. The aluminium foil (anode foil) obtained in this manner is then provided with a contact wire and wound up with a further optionally porous aluminium foil (cathode foil) likewise provided with a contact wire, these two foils being spaced from one another by one or more separators, which are based e.g., on cellulose or, preferably, on synthetic papers. After being wound up, the anode bodies obtained in this way are fixed, for example by means of an adhesive tape. The separator or separators can be carbonized by heating in an oven. This method and manner of production of anode bodies for aluminium wound capacitors is adequately known from the prior art and is described, for example, in U.S. Pat. No. 7,497,879 B2.

According to further particular embodiments of process 2 according to the invention, the electrolyte capacitor to be produced is an aluminium stacked capacitor or a tantalum electrolytic capacitor ("tantalum elco"), in particular a tantalum electrolytic capacitor having a polymeric outer layer, such as is described in DE-A-10 2009 007 594.

In process step II) of process 2 according to the invention, liquid composition 1 or 2 according to the present invention is introduced into at least a part of the anode body. In this context it should be noted that, before introducing liquid composition 1 or 2 into at least a part of the anode body, other compositions may be introduced into the anode body for the formation of an electrically conductive layer, such as a PEDOT/PSS-dispersion. It is therefore not necessarily required to directly apply liquid composition 1 or 2 onto at least a part of the dielectric layer of the anode body.

Liquid composition 1 or 2 is introduced into the porous region by known processes, e.g., impregnation, dipping, pouring, dripping on, spraying, misting on, knife coating, brushing or printing, for example ink-jet, screen or tampon printing. Preferably, the introduction is carried out by dipping the anode body into the liquid composition and thus impregnating it with this liquid composition. The dipping into or the impregnation with the liquid composition is preferably carried out for a period in a range of from 1 second to 120 minutes, particularly preferably in a range of from 5 seconds to 60 minutes and most preferably in a range of from 10 seconds to 15 minutes. The introduction of the liquid composition into the anode body can be facilitated, for example, by increased or reduced pressure, vibration, ultrasound or heat.

Liquid composition 1 or 2 employed in process step II) can, besides the functionalized π-conjugated polymer a), the solvent c) and optionally a reminder of the oxidizing agent b) in its reduced form, moreover comprise further additives, such as surface-active substances, e.g. anionic surfactants, such as e.g. alkylbenzenesulphonic acids and salts, paraffin sulphonates, alcohol sulphonates, ether sulphonates, sulphosuccinates, phosphate esters, alkyl ether carboxylic acids or carboxylates, cationic surfactants, such as e.g. quaternary alkylammonium salts, nonionic surfactants, such as e.g. linear alcohol ethoxylates, oxo alcohol ethoxylates, alkylphenol ethoxylates or alkyl polyglucosides, in particular surfactants that are commercially available under the trademarks Dynol® and Zonyl®, or adhesion promoters, such as e.g. organofunctional silanes or hydrolysates thereof, e.g. 3-glycidoxypropyltrialkoxysilane, 3-aminopropyl-triethoxysilane, 3-mercaptopropyltrimethoxysilane, 3-methacryloxypropyltrimethoxy-silane, vinyltrimethoxysilane or octyltriethoxysilane, crosslinking agents, such as melamine compounds, masked isocyanates, functional silanes—e.g. tetraethoxysilane, alkoxysilane hydrolysates, e.g. based on tetraethoxysilane, epoxysilanes, such as 3-glycidoxypropyltrialkoxysilane-polyurethanes, polyacrylates or polyolefin dispersions.

Preferably, liquid composition 1 or 2 employed in process step II) comprise further additives which optionally increase the conductivity, such as e.g. compounds containing ether groups, such as e.g. tetrahydrofuran, compounds containing lactone groups, such as γ-butyrolactone, γ-valerolactone, compounds containing amide or lactam groups, such as caprolactam, N-methyl-caprolactam, N,N-dimethylacetamide, N-methylacetamide, N,N-dimethylformamide (DMF), N-methylformamide, N-methylformanilide, N-methylpyrrolidone (NMP), N-octylpyrrolidone, pyrrolidone, sulphones and sulphoxides, such as e.g. sulpholane (tetramethylene sulphone), dimethylsulphoxide (DMSO), sugars or sugar derivatives, such as e.g. sucrose, glucose, fructose, lactose, sugar alcohols, such as e.g. sorbitol, mannitol, furan derivatives, such as e.g. 2-furancarboxylic acid, 3-furancarboxylic acid, glycerol, diglycerol, triglycerol or tetraglycerol.

Liquid composition 1 or 2 employed in process step II) can moreover comprise as a further additive one or more organic binders which are soluble in organic solvents, as described in WO 2009/141209 A1 on page 12, lines 16-34.

In this context it is, however, particularly preferred that the above mentioned further additives are added to the liquid composition before in process step ii) of process 1 according to the present invention in the pH-value has been adjusted to be within the range from 2.5 to 10 by the addition of a base.

The viscosity of liquid composition 1 or 2 employed in process step II) can be between 0.01 and 1,000 mPa·s (measured with a rheometer at 20° C. and a shear rate of 100 s$^{-1}$), depending on the method of application. Preferably, the viscosity is 1 to 500 mPa·s, particularly preferably between 1 to 250 mPa·s. In the case of the production of aluminium wound capacitors the viscosity is very particularly preferably in a range of from 1 to 200 mPa·s, while in the production of tantalum electrolytic capacitors or aluminium stacked capacitors it is very particularly preferably in a range of from 1 to 50 mPa·s. The adjustment of the viscosity can, for example, be accomplished by adding appropriate rheology modifiers as a further additive.

The solids content of liquid composition 1 or 2 employed in process step II) is preferably in a range of from 0.01 to 20 wt.-%, particularly preferably in a range of from 0.1 to 15 wt.-% and most preferably in a range of from 0.25 to 10 wt.-%, in each case based on the total weight of the liquid composition. The solids content of the liquid composition is determined via drying of the liquid composition at a temperature which is sufficiently high to remove the solvent c).

According to a particularly preferred embodiment of process 2 according to the present invention liquid composition 1 or 2 that is introduced into the capacitor body not only comprises the functionalized π-conjugated polymer, but-in addition to this self-doped conductive polymers foreign doped conductive polymer, preferably PEDOT/PSS, as disclosed in WO 2014/048562 A2. The disclosure of WO 2014/048562 A2 regarding the combined use of self-doped polymers like PEDOT-S and foreign-doped polymers like PEDOT/PSS for the formation of a solid electrolyte is incorporated herein by reference and forms a part of the disclosure of the present application.

After the anode bodies have been impregnated with liquid composition 1 or 2 according to the present invention as described above, it is advantageous to at least partially remove the solvent c) contained in the liquid composition in a subsequent process step III), so that a solid electrolyte which completely or partly covers the dielectric, and therefore a capacitor body is formed. In this context it is preferable for the covering of the dielectric by the solid electrolyte to be preferably at least 10%, particularly preferably at least 25% and most preferably at least 50%, it being possible for the covering to be determined by measurement of the capacitance of the capacitor in the dry and in the damp state at 120 Hz, as is described in DE-A-10 2005 043 828.

The removal or hardening is preferably carried out by removing the electrode body from the liquid composition and drying it, the drying preferably being carried out at a temperature in a range of from 20° C. to 260° C., particularly preferably in a range of from 50° C. to 220° C. and most preferably in a range of from 80° C. to 200° C. It is, of course, also possible to at least partially remove the solvent c) by freeze drying. Process steps II) and III) can also be repeated once or several times, in order in this manner to adapt the thickness of the layer of the solid electrolyte deposited on the dielectric or the degree of filling of the electrolyte in the electrode body to the particular requirements.

After the capacitor bodies have been produced in this manner, they can be further modified by the method and manner known to the person skilled in the art. In the case of a tantalum electrolytic capacitor, the capacitor bodies can be covered, for example, with a polymeric outer layer, as is described in DE-A-10 2004 022674 or DE-A-10 2009 007 594, and/or a graphite layer and a silver layer, as is known from DE-A-10 2005 043 828, while in the case of an aluminium wound capacitor, in accordance with the teaching of U.S. Pat. No. 7,497,879 B2, the capacitor body is incorporated into an aluminium beaker, provided with a sealing glass and firmly closed mechanically by crimping. The capacitor can then be freed from defects in the dielectric in a known manner by ageing.

The invention is now explained in more detail with the aid of non-limiting figures and examples.

FIG. 1 is a diagram of a section through a part of a capacitor obtainable by the process according to the invention for the production of a capacitor. This has an electrode body 1, usually made of a porous electrode material 2, such as aluminium or tantalum. On the surface 4 of the electrode material 2, a dielectric 3 is formed as a thin layer, so that an anode body 5 which is still porous and comprises the electrode body 1 of the electrode material 2 and the dielectric 3 is formed. The dielectric 3 is followed, optionally after further layers, by a layer of a solid electrolyte 6 (e.g., a layer that has been prepared using liquid composition 1 or 2 according to the present invention), whereby a capacitor body 7 comprising the electrode body 1 of the electrode material 2, the dielectric 3 and the solid electrolyte 6 is formed.

TEST METHODS

Equivalent Series Resistance (ESR)

Figure 1:
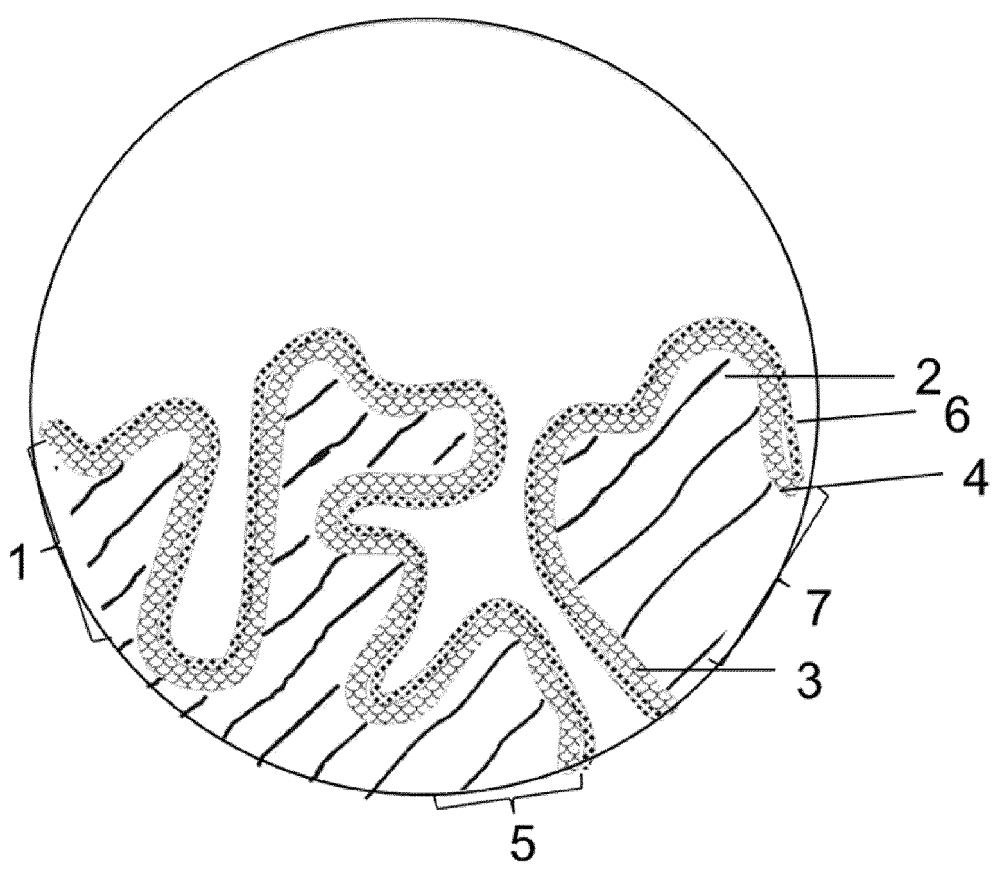

The equivalent series resistance (in m$\Omega$) was determined at 20° C. at 100 kHz by means of an LCR meter (Agilent 4284A). In each capacitor experiment at least 5 capacitors have been prepared and the average ESR-value was determined.

Thermal Stability

The thermal stability is determined by means of thermogravimetric analysis (TGA).

The TGA of solid samples is conducted with a TGA/DSC 2 LF/1100 from Mettler Toledo. About 10 g of the polymer dispersion of interest is dried at 100° C. for 16 h in a vacuum oven at 50 mbar in a beaker with a diameter of at least 3 cm to remove all solvents. About 15 mg of a solid conductive polymer is introduced into a measuring vial and the vial is placed in the support of the instrument.

The sample is first heated from room temperature to 100° C. The sample is kept then at 100° C. for 30 min under N$_2$ to dry the sample. The sample is subsequently heated in a second heating scan without exposing the sample to air from 100° C. to 600° C. at a constant heating rate of 5 K/min. The weight of the sample is simultaneously monitored while heating.

The monitored weight loss of the sample over time is converted in a diagram of weight loss over temperature. The data are normalized to 100 wt. % at 100° C. Additionally, the derivative of the data is calculated, by forming the ratio of the differential change of mass in weight % and unit time.

Conductivity

A cleaned glass substrate was laid on a spin coater and 10 ml of the liquid composition according to the invention was distributed over the substrate. The remaining solution was then spun off by rotation of the plate. Thereafter, the substrate thus coated was dried for 15 minutes at 130° C. on a hot plate. The layer thickness was then determined by means of a layer thickness measuring device. (Tencor, Alphastep 500). The conductivity was determined in that Ag electrodes of 2.5 cm length were vapour deposited at a distance of 10 mm via a shadow mask. The surface resistance determined with an electrometer (Keithly 614) was multiplied by the layer thickness in order to obtain the specific electrical resistivity. The conductivity is the inverse of the specific electrical resistivity.

Average

If not otherwise mentioned, the average corresponds to the arithmetical average value.

EXAMPLES

Example 1 (Preparation of a PEDOT-S-Dispersion)

A 3 L jacketed tank made of stainless steel is equipped a mechanical stirrer, a ventilation valve at the upper lid, a material inlet that can be closed and a thermometer.

Component A

Into this tank 2000 g of deionized water, 16.0 g of a 10 wt.-% aqueous iron (III) sulfate solution, 5.7 g sulfuric acid (95 wt.-%) and 100 g of EDOT-S sodium salt (0.29 mol) were introduced. The stirrer was operated at 50 rpm, the temperature was adjusted to 20° C. and the inner pressure was reduced to 100 hPa. The pressure in the tank was subsequently raised to atmospheric pressure, followed by a further reduction of a pressure to 25 hPa in order to expel the oxygen.

Component B

In a separate glass beaker 78.5 g sodium peroxodisulfate were dissolved in 200 ml water and nitrogen was blown through the solution for 30 minutes while stirring until the oxygen content was below 0.25 mg/l.

Component B was then sucked into the tank. The material inlet was then closed and the inner pressure of the tank was adjusted to 25 hPa by means of a vacuum pump. The initial pH of the reaction solution was 1.9 and the reaction was continued for 19 hours under this reduced pressure. After the reaction was completed, the reaction mixture was filled up to a volume of 10 L by adding deionized water and was subsequently treated by means of ultrafiltration (Pall Microza SLP 1053 with a cut-off of 10000 g/mol), whereby 8 L of water were removed. This procedure was repeated 6 times in order to remove the inorganic salts.

The thus obtained composition was characterized by a conductivity of 72 S/cm and a solid content of 1.22 wt. %. The composition was further concentrated by means of ultra-filtration until a solid content of 2.4 wt. % was reached. The thus obtained PEDOT-S-dispersion is subsequently referred to as "sample #1")

Example 2 (Adjustment of pH-Value by Means of NaOH; Samples #2-#7, #21-#25)

A 100 ml beaker is filled with about 50 ml of sample #1. A 10 wt. % aqueous NaOH-solution is prepared and added dropwise to sample #1 while stirring until the solution has reached the desired pH. The pH of the solution is monitored with a pH-Meter (Model 766 Calimatic, Knick) while adding the base.

Example 3 (Adjustment of pH-Value by Means of LiOH; Sample #8)

Preparation as in Example 2 with the difference that a 10 wt. % aqueous LiOH-solution is added to adjust the pH.

Example 4 (Adjustment of pH-Value by Means of KOH; Samples #9 and #11)

Preparation as in Example 2 with the difference that a 10 wt. % aqueous KOH-solution is added to adjust the pH.

Example 5 (Adjustment of pH-Value by Means of $NH_4OH$; Samples #10 and #12)

Preparation as in Example 2 with the difference that a 10 wt. % aqueous $NH_4OH$-solution is added to adjust the pH.

Example 6 (Adjustment of pH-Value by Means of DMAH; Sample #13)

Preparation as in Example 2 with the difference that a 10 wt. % aqueous dimethylaminoethanol (DMAE)-solution is added to adjust the pH.

Figure 2:
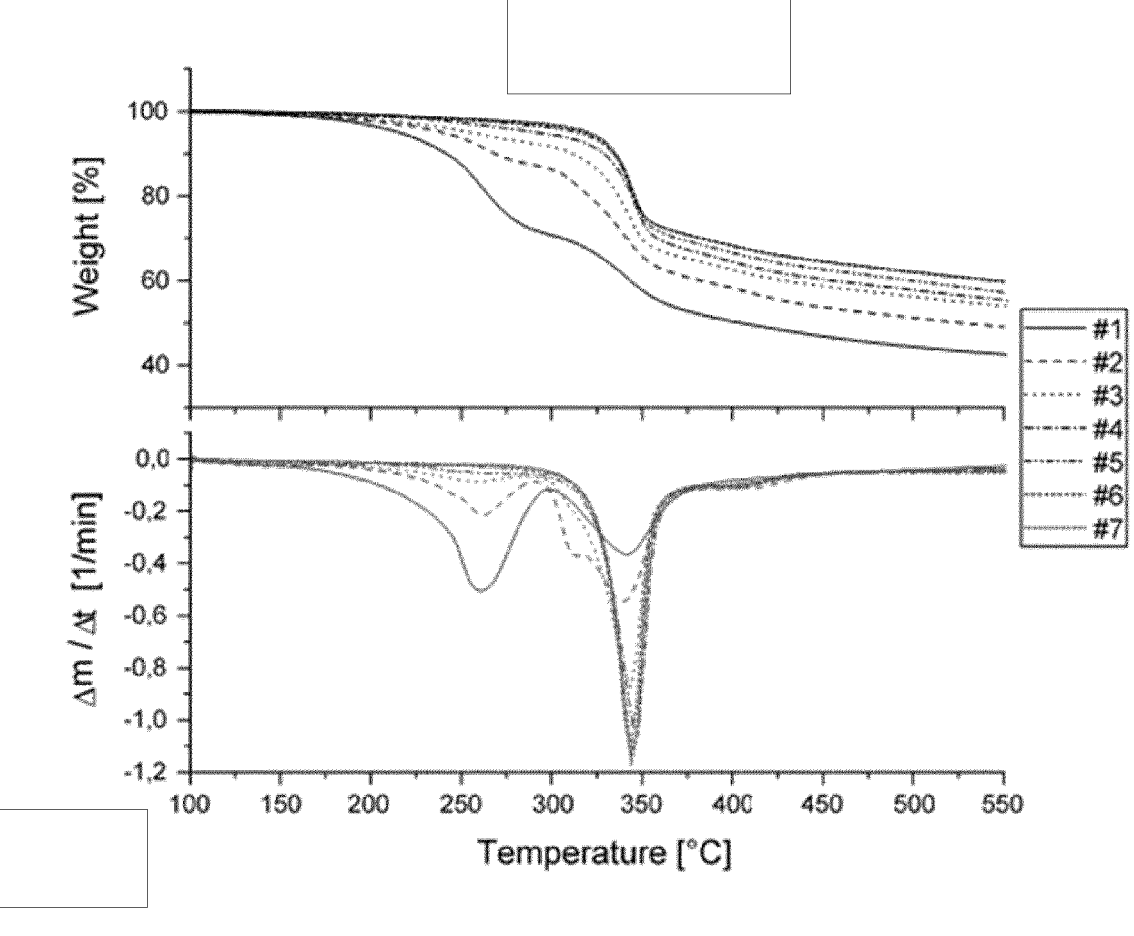
FIG. 2 is a TGA-diagram showing the weight-loss over temperature in the upper diagram for samples #1-#7. The lower diagram depicts the derivatives of weight vs. time scans.
Figure 3:
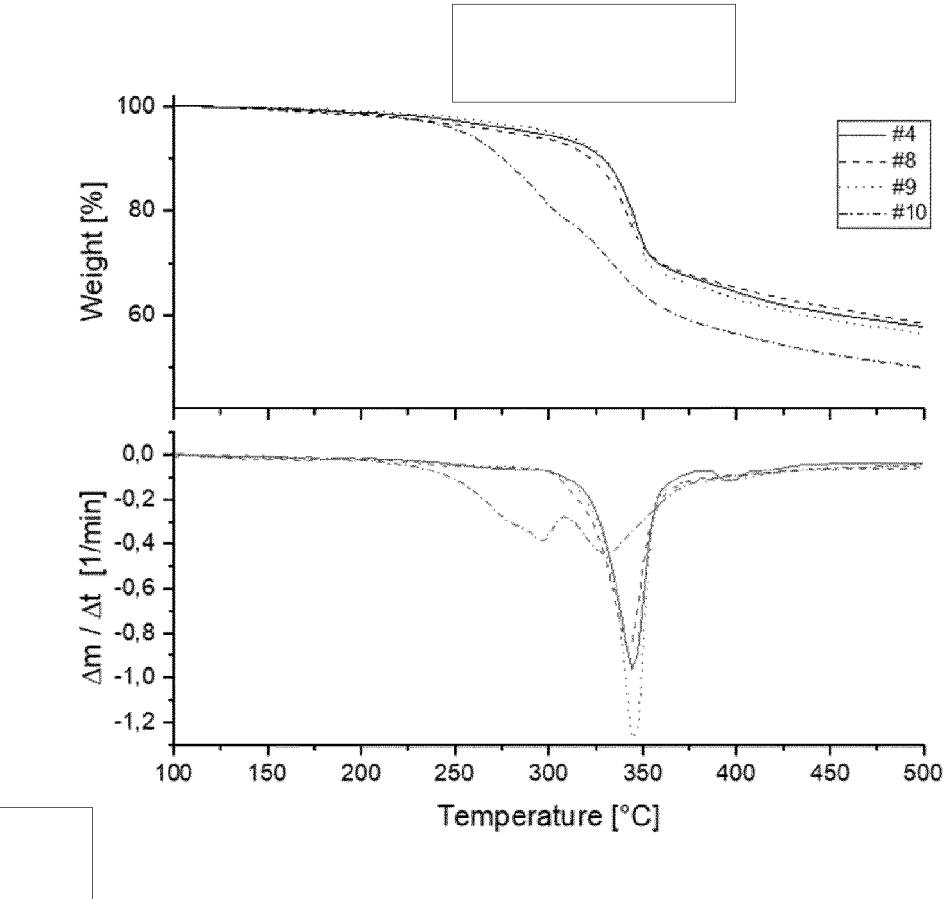
FIG. 3 is a TGA-diagram showing the weight-loss over temperature in the upper diagram for samples #4, #8, #9 and #10. The lower diagram depicts the derivatives of weight vs. time scans.
Figure 4:
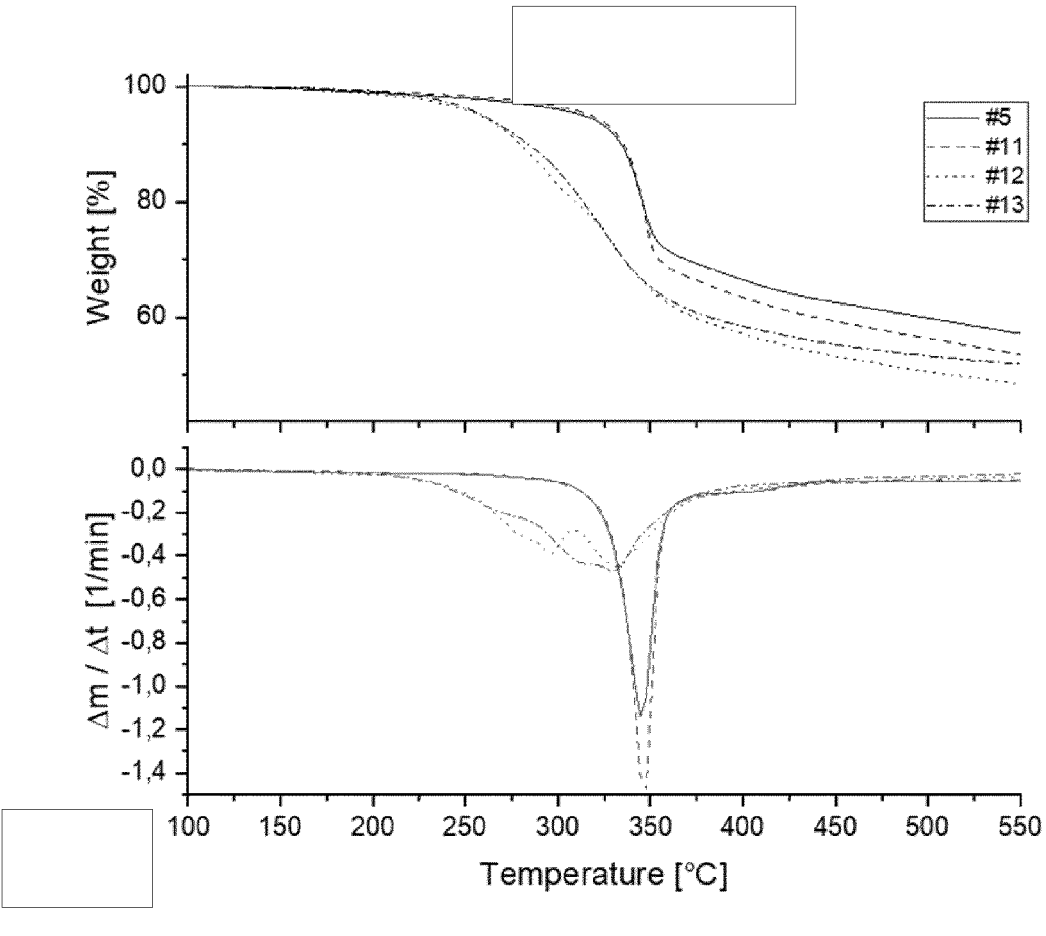
FIG. 4 is a TGA-diagram showing the weight-loss over temperature in the upper diagram for samples #5, #11, #12 and #13. The lower diagram depicts the derivatives of weight vs. time scans.

The TGA-diagrams of samples #1-#13 are outlined in FIG. 2, FIG. 3 and FIG. 4 depicting the weight-loss over temperature in the upper diagram each. The lower diagram depicts the derivatives of weight vs. time scans.

Table 1 displays in columns 5-8 the temperatures that correspond to a sample-weight of 100%, 90%, 80% and 70% as being extracted from the weight vs. temperature—data in FIG. 2-4. The peak positions of the 1. peak at about 261° C. and 2. peak is at about 345° C. are extracted from the derivative-plots in FIG. 2-4 when assignable.

TABLE 1

| | | | | sample weight [wt.-%] | | | | | | | | |
|---|---|---|---|---|---|---|---|---|---|---|---|---|
| | | | | 100 | 90 | 80 | 70 | T1[1] | DV1[2] | T2[3] | DV2[4] | ratio |
| | sample | base | pH | temperature [° C.] | | | | [° C.] | [1/min] | [° C.] | [1/min] | DV1/DV2 |
| FIG. 2 | #1 | | 1.8 | 100 | 242 | 265 | 306 | 261 | −0.51 | 341 | −0.37 | 1.378 |
| | #2 | NaOH | 2.1 | 100 | 269 | 321 | 341 | 261 | −0.22 | 341 | −0.55 | 0.400 |
| | #3 | NaOH | 2.5 | 100 | 311 | 337 | 350 | 261 | −0.087 | 344 | −0.88 | 0.099 |
| | #4 | NaOH | 3 | 100 | 329 | 344 | 358 | n.d. | −0.055 | 345 | −1.02 | 0.054 |
| | #5 | NaOH | 6 | 100 | 334 | 346 | 370 | n.d. | −0.03 | 345 | −1.14 | 0.026 |
| | #6 | NaOH | 8 | 100 | 334 | 345 | 383 | n.d. | −0.025 | 344 | −1.17 | 0.021 |
| | #7 | NaOH | 10 | 100 | 346 | 346 | 382 | n.d. | −0.025 | 344 | −1.13 | 0.022 |
| FIG. 3 | #4 | NaOH | 3 | 100 | 329 | 344 | 358 | n.d. | −0.055 | 345 | −1.02 | 0.054 |
| | #8 | LiOH | 3 | 100 | 322 | 341 | 360 | n.d. | −0.052 | 343 | −0.86 | 0.060 |
| | #9 | KOH | 3 | 100 | 330 | 344 | 353 | n.d. | −0.048 | 344 | −1.27 | 0.038 |
| | #10 | $NH_3$ | 3 | 100 | 275 | 303 | 334 | 261 | −2.000 | 334 | −0.40 | 5.000 |
| FIG. 4 | #5 | NaOH | 6 | 100 | 334 | 346 | 370 | n.d. | −0.03 | 345 | −1.14 | 0.026 |
| | #11 | KOH | 6 | 100 | 336 | 345 | 355 | n.d. | −0.027 | 348 | −1.47 | 0.018 |
| | #12 | $NH_3$ | 6 | 100 | 280 | 310 | 336 | 261 | −0.173 | 331 | −0.45 | 0.384 |
| | #13 | DMAH | 6 | 100 | 284 | 314 | 336 | 261 | −0.172 | 331 | −0.46 | 0.374 |

[1]T1 = temperature at the 1st peak
[2]DV1 = derivative value at 261° C.
[3]T2 = temperature at the 2nd peak
[4]DV2 = derivative value of the 2nd peak

Example 7 (Preparation of a Capacitor)

Tantalum powder having a specific capacitance of 30000 CV/g was pressed to pellets with inclusion of a tantalum wire and sintered in order to form a porous anode body having dimensions of 1.4 mm×2.8 mm×3.9 mm. 5 of these porous electrode bodies were anodized in a phosphoric acid electrolyte at 60 V to form a dielectric, in order to obtain the anode bodies.

The anode bodies were impregnated in sample #3 for 1 min. Thereafter, drying was carried out at 120° C. for 10 min.

Next the anode bodies were impregnated in a PEDOT:PSS dispersion (Clevios K Nano LV, Heraeus) for 1 min. Thereafter, drying was carried out at 120° C. for 10 min. The impregnation and drying were carried out nine further times.

Next the anode bodies were dipped in a crosslinker solution (Clevios K Primer W5, Heraeus), dried at 120° C. for 10 min and thereafter dipped in a PEDOT:PSS dispersion (Clevios K V2 HV, Heraeus) and dried at 120° C. for 10 min. This sequential dip and dry in crosslinker and PEDOT:PSS dispersion was repeated additional two times.

Finally, the anode bodies were covered with a graphite layer and thereafter with a silver layer in order to obtain the finished capacitors in this way.

The mean values for ESR were determined before and after exposure of the capacitors to 125° C. for 100 hours. The relative increase in ESR is calculated as relative ESR increase=[ESR (after exposure to 125° C.)–ESR (before exposure to 125° C.)]/ESR (before exposure to 125° C.). The value of the relative ESR increase in % is shown in Table 2.

Example 8

Capacitors were prepared the same way as in Example 7 except that sample #4 instead of sample #3 was used.

Example 9

Capacitors were prepared the same way as in Example 7 except that sample #5 instead of sample #3 was used.

Example 10

Capacitors were prepared the same way as in Example 7 except that sample #6 instead of sample #3 was used.

Example 11

Capacitors were prepared the same way as in Example 7 except that sample #8 instead of sample #3 was used.

Example 12

Capacitors were prepared the same way as in Example 7 except that sample #11 instead of sample #3 was used.

Example 13

Capacitors were prepared the same way as in Example 7 except that sample #12 instead of sample #4 was used.

Example 14

Capacitors were prepared the same way as in Example 7 except that sample #1 instead of sample #3 was used.

TABLE 2

| | relative ESR increase |
| --- | --- |
| Example 7 (pH = 2.5; NaOH) | 20% |
| Example 8 (pH = 3; NaOH) | 11% |
| Example 9 (pH = 6; NaOH) | 13% |
| Example 10 (pH = 8; NaOH) | 17% |
| Example 11 (pH = 3; LiOH) | 13% |
| Example 12 (pH = 6; KOH) | 11% |
| Example 13 (pH = 6; $NH_3$) | 43% |
| Example 14 (pH = 1.8) | 89% |

The invention claimed is:

1. A liquid composition comprising functionalized $\pi$-conjugated polythiophenes obtained by a process comprising the steps of:

i) providing a liquid phase comprising a functionalized $\pi$-conjugated polythiophene that is dissolved or dispersed in a solvent, wherein the functionalized $\pi$-conjugated polythiophene comprises repeating units of the general formula (I)

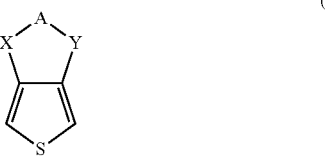

(I)

wherein

X, Y are identical or different and are O, S, or $NR^1$, wherein $R^1$ is hydrogen or an aliphatic or aromatic residue having 1 to 18 carbon atoms;

A is an organic residue carrying an anionic functional group; and wherein the liquid phase has a pH-value of less than 2.5; and ii) adjusting the pH-value of the liquid phase provided in process step i) to a value in the range from 6 to 8 by adding an alkali metal hydroxide.

2. A liquid composition having a pH-value in the range from 6 to 8 and comprising an alkali metal hydroxide and a functionalized $\pi$-conjugated polythiophene that is dissolved or dispersed in a solvent, wherein the polythiophene comprises repeating units of the general formula (I):

(I)

wherein X, Y are identical or different and are O, S, or $NR^1$, wherein $R^1$ is hydrogen or an aliphatic or aromatic residue having 1 to 18 carbon atoms;

A is an organic residue carrying an anionic functional group;

and wherein a composition that is obtained after drying the liquid composition at a temperature of 100° C. and a pressure of 50 mbar for 16 hours, fulfills at least one of the following conditions (A) to (E):

(A) a weight loss of 10 wt.-%, based on the total weight of the dried liquid composition, at a temperature of not less than 300° C. as determined by means of thermogravimetric analysis;

(B) a weight loss of 20 wt.-%, based on the total weight of the dried liquid composition, at a temperature of not less than 330° C. as determined by means of thermogravimetric analysis;

(C) a weight loss of 30 wt.-%, based on the total weight of the dried liquid composition, at a temperature of not less than 345° C. as determined by means of thermogravimetric analysis;

(D) absence of a peak in a derivative plot of weight versus time from a thermogravimetric analysis in the interval between 250° C. and 270° C.;

(E) a ratio of a derivative value at 261° C. to the derivative value at a $2^{nd}$ peak of 0.01 or less.

3. A liquid composition comprising a liquid phase comprising a functionalized π-conjugate polythiophene that is dissolved or dispersed in a solvent, wherein the functionalized π-conjugate polythiophene comprises repeating units of the general formula (I):

(I)

15 wherein

X, Y are identical or different and are O, S, or NR$^1$, wherein R$^1$ is hydrogen or an aliphatic or aromatic residue having 1 to 18 carbon atoms;

A is an organic residue carrying an anionic functional group;

and wherein the liquid phase comprises an alkali metal hydroxide and has a pH value in the range from 6 to 8.

\*    \*    \*    \*    \*